US00PP09169P

United States Patent [19]

Lamb et al.

[11] Patent Number: Plant 9,169

[45] Date of Patent: Jun. 13, 1995

[54] ANTHURIUM PLANT NAMED 'SHAZZAM'

[75] Inventors: Ann E. Lamb, Sebring; Robert D. Hartman, Lake Placid, both of Fla.

[73] Assignee: Twyford International Inc., Sebring, Fla.

[21] Appl. No.: 286,237

[22] Filed: Aug. 8, 1994

[51] Int. Cl.[6] ..... A01H 5/00

[52] U.S. Cl. ..... Plt./88.1

[58] Field of Search ..... Plt. 88.1

*Primary Examiner*—James R. Feyrer

*Attorney, Agent, or Firm*—Foley & Lardner

[57] ABSTRACT

A new and distinct Anthurium plant named Shazzam characterized by its bright red-orange, cupped, round or elliptical spathes and red-orange spadix; immature leaves are yellow to light green with a bronze cast, maturing to a solid medium green; leaves are relatively long and leathery; attractive compact habit, and tolerance to heat and disease.

1 Drawing Sheet

The present invention comprises a new and distinct cultivar of Anthurium, botanically known as *Anthurium scherzerianum,* and referred to by the cultivar name Shazzam.

The new cultivar is a product of a breeding program carried out by the inventors Ann E. Lamb and Robert D. Hartman. The seedling is a result of a cross of unknown parentage made in Palmdale, Fla. The cultivar was discovered from the progeny of the stated cross in Palmdale, Fla. by Ann E. Lamb. Asexual propagation by tissue culture carried out in Palmdale, Fla. by or under the supervision of the inventors has demonstrated the stability of the combination of characteristics of its new cultivar from generation to generation.

The following observations, measurements, and values describe plants grown in Apopka, Fla. under shadehouse conditions which closely approximate those generally used in horticultural practice.

The following traits have been repeatedly observed to be characteristics which in combination distinguish Shazzam as a unique new cultivar.

1. The plant produces large cupped elliptical spathes, with the spadix often being twisted.
2. The spathes are held above and among the foliage.
3. The spathes are red-orange in color. The spadix is orange.
4. The leaves are long, leathery, and medium green when mature. Immature leaves are yellow to light green with a bronze cast, with two immature leaves being shown in the color photographic drawing.
5. The plant habit is compact.
6. The plant was selected for its tolerance to heat and disease.

All color references are measured against the Royal Horticultural Society Colour Chart. Colors are approximate as color depends on horticultural practices such as light level and fertilization rate, among others, without, however, any change in genotype.

The color photographic drawing comprises a top perspective view of the inflorescence and foliage of a plant of Shazzam in a 10.2 cm pot.

The photographs were taken approximately 30 weeks after planting a 20 week old liner obtained by tissue culture and grown under appropriate growing conditions. Colors are as accurate as possible with color illustrations of this type.

Origin: Seedling of unknown parentage.

Classification:

*Botanical.*—*Anthurium scherzerianum* cv. Shazzam.

Propagation: Asexual production either by tissue culture or division.

Inflorescence (Spathe)

Immature spathe: Spathe is tightly rolled around the spadix and extrudes from the petiole speath. The spathe is fully open when the pedicel is fully elongated, approximately 16 cm above the soil surface. The color of the pedicel is greener than 173A, with an anthocyanous cast.

Mature spathe:

*Size.*—The flattened spathe is approximately 7.1 cm to 8.4 cm long and approximately 7.0 cm to 8.2 cm in width.

*Color.*—Fully open: Upper surface is 44A; lower surface is 44B. Mature: Upper surface is 43A; lower surface is 43B.

*Arrangement.*—The spathe stands up on wiry pedicels and opens above the leaves.

*Shape.*—The spathe is elliptical to round with an obtuse to cordate base and a cuspidate tip that is slightly hooked. It is distinctly cupped or twisted and approximately 6.5 cm to 8.4 cm in length, 6.2 cm to 7.0 cm in width, and 1.8 cm in depth. The spathe may reflex as it ages.

*Flowering time.*—After approximately 8 months from a 20 week old liner for an untreated plant as illustrated in photograph, and depending on season, approximately 1 to 4 blossoms will be present. Smaller blossoms may occur on less mature growth. First flowers (1 to 2) can be expected approximately 4–5 months after planting a 20 week old liner.

Reproductive organs:

*Spadix.*—Size: Approximately 4.0 cm to 5.2 cm in length and 5.5 mm in width. Color: 33A. Stamens: Anthers and filaments are not clearly visible. Pollen: 10D in color. Pistil: Translucent 33D in color, protruding between the staminate flowers, firmly fixed to the main axil. The pistilate flowers extend approximately 0.5 mm beyond the staminate flowers. Roots: White fleshy roots with fine laterals.

Plant:

General appearance: When a 20 week old liner is grown in a 10.2 cm pot for 30 weeks under appropriate growing conditions, Shazzam is approximately 16 cm to 20 cm in height and approximately 34 cm to 38 cm in width.

Leaves:

*Form.*—The leaf blade is ovate with a acuminate tip and a cordate base. The margins are entire. The midrib is straight over the length of the leaf. The leaf blade is distinctly folded upward from the midrib. The leaf margin is straight.

*Size.*—Leaf blades of a mature-sized plant are approximately 14 cm to 17 cm in length and approximately 5 cm to 6.5 cm in width.

*Petiole.*—The petiole is approximately 10.2 cm to 12.4 cm in height from the base of the petiole to the base of the leaf blade on the primary shoot. Secondary shoots are somewhat smaller depending on the age of the shoot. The petiole is approximately 3.0 mm in diameter just below the geniculum, and straight. Two parallel ridges run the length of the upper surface of the petiole.

*Petiole wings.*—Petiole wings are approximately 0.9 cm to 1.7 cm in length and approximately 3.0 mm in width at their midpoint. The tips of the petiole wings are rounded. There is approximately 8.3 cm to 9.1 cm between the top of the wing and the base of the geniculum.

*Geniculum.*—The geniculum is approximately 10 mm to 12 mm in length, and approximately 4.5 mm in diameter. The color is 145A. If grown in bright light, the exposed surface becomes anthocyanous. There is no space between the top of the geniculum and the base of the leaf blade. The geniculum is prominent.

*Veins.*—Veins are sunken, with the leaf blade slightly convex or flat between veins on the upper surface. The midrib protrudes from the upper surface of the leaf for approximately ¾ the length of the leaf. There are two primary veins bordering the perimeter of the leaf.

*Lobes.*—The leaf has two rounded lobes which extend past the petiole. The distance from the petiole/leaf juncture to the highest point on the lobes is approximately 1.3 cm.

*Color.*—Immature leaves are yellow to light green with a bronze cast (see photo); mature leaves are 147A-B on upper surface and 146B on lower surface. Midrib, upper surface is 147B and lower surface is 146C. Petiole is 146B and petiole wing is 146C, bordered with 183B.

I claim:

1. A new and distinct cultivar of Anthurium plant named Shazzam, as illustrated and described.

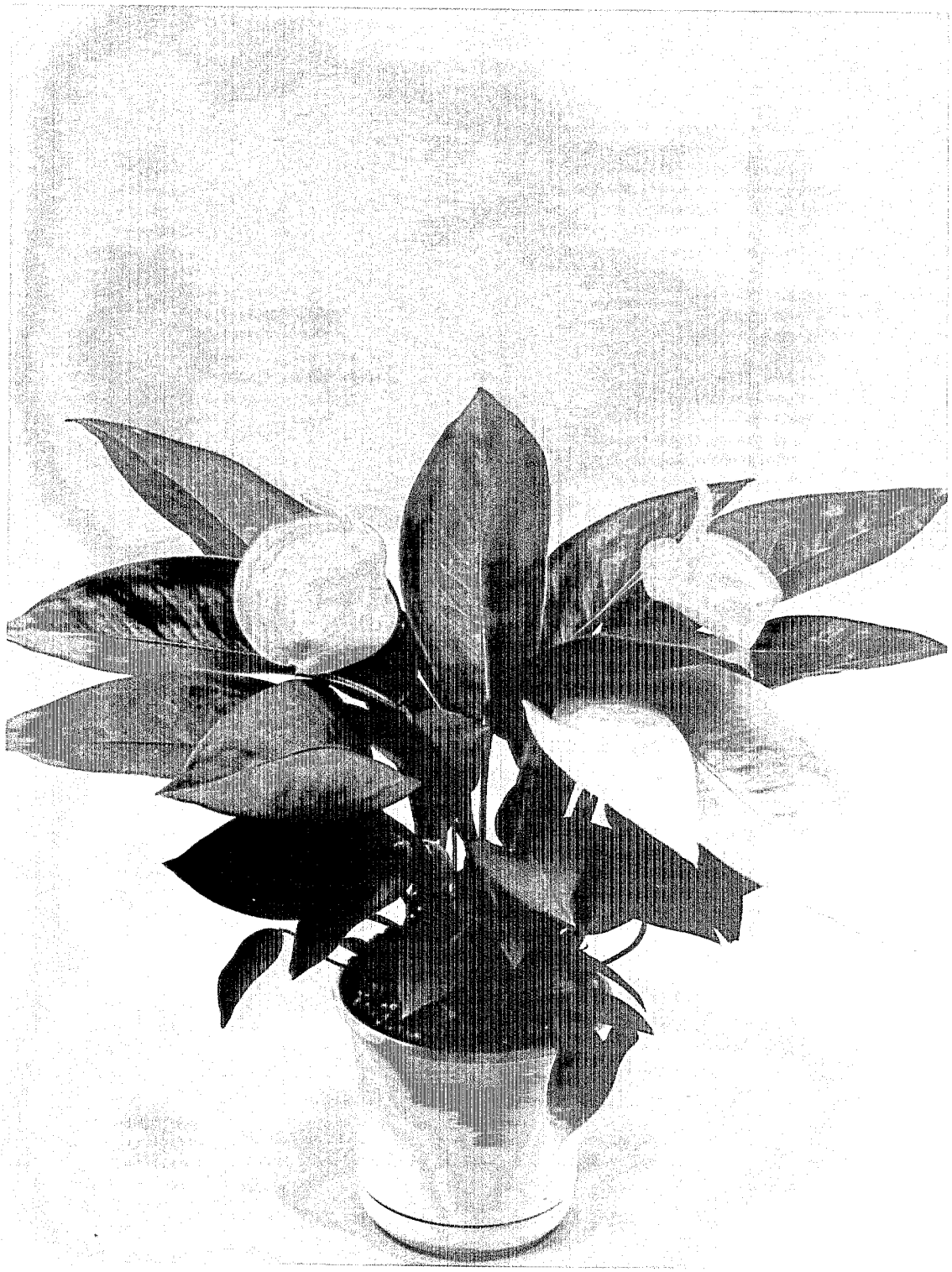

* * * * *